United States Patent [19]

DeVries et al.

[11] Patent Number: 4,596,548
[45] Date of Patent: Jun. 24, 1986

[54] SINGLE STAGE VENOUS CATHETER

[75] Inventors: James H. DeVries, Grand Rapids; Ronald A. Williams, Caledonia, both of Mich.

[73] Assignee: DLP Inc., Grand Rapids, Mich.

[21] Appl. No.: 715,727

[22] Filed: Mar. 25, 1985

[51] Int. Cl.[4] .............................. A61M 25/00
[52] U.S. Cl. ................................ 604/4; 604/43; 604/93; 604/264
[58] Field of Search ............... 604/4, 43, 49–53, 604/93, 264, 280–284

[56] References Cited

U.S. PATENT DOCUMENTS 4,129,129 12/1978 Amrine ...................... 604/43 X
4,248,224 2/1981 Jones ........................ 604/284 X
4,309,994 1/1982 Grunwald .................... 604/284 X
4,398,910 8/1983 Blake et al. ................. 604/93

FOREIGN PATENT DOCUMENTS 105038 3/1917 United Kingdom ................ 604/93

Primary Examiner—Dalton L. Truluck
Attorney, Agent, or Firm—Barnes, Kisselle, Raisch, Choate, Whittemore & Hulbert

[57] ABSTRACT

A single stage venous catheter for use in open heart surgery which has an extended insertion end provided with axially extending open-sided sectorial grooves around a common axis, the grooves terminating in a common receiving chamber surrounded by circumferentially spaced multiple fins or ribs to maintain the proper clearance for the catheter chamber.

5 Claims, 8 Drawing Figures

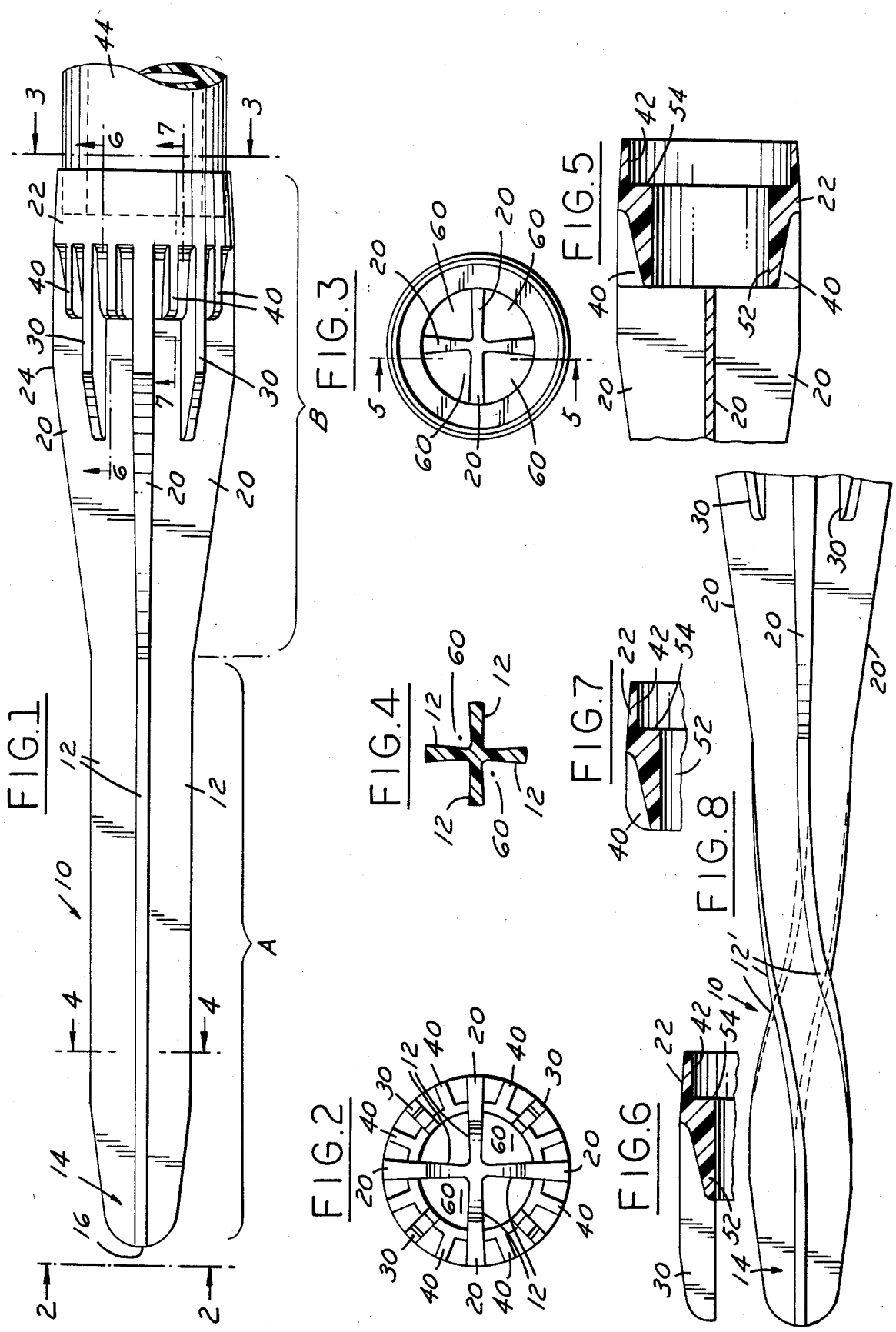

ical variations and intra-operative manipulation of the heart may cause a reduction in venous drainage due to distortion of the atrial walls and vena cava or shifting of the catheter position.

SINGLE STAGE VENOUS CATHETER

FIELD OF INVENTION

Catheters for introduction to the heart organ during open heart surgery.

BACKGROUND AND OBJECTS OF THE INVENTION

In heart surgery, life support machines are utilized to perform temporarily the function of the heart and lungs while the patient's heart is being surgically serviced such as the repair of heart wall lesions, installation of a valve, and by-pass artery work. The life support machine must take the flowing blood from the patient, maintain the temperature, pressure, and flow rate within certain physiologic limits, and provide the lung function.

In the course of an operation of this type, it is essential that a change-over be accomplished from the natural heart function to the machine. This involves installation of a venous return catheter into the right atrium (chamber) of the heart to serve as a drainage supply connection to the pumping machine. Experience has shown that, when used in certain procedures such as coronary artery by-pass to the circumflex coronary artery, anatomical variations and intra-operative manipulation of the heart may cause a reduction in venous drainage due to distortion of the atrial walls and vena cava or shifting of the catheter position.

The traditional method of venous drainage has been to place two catheters, one into the superior vena cava. This method provides good venous return in all operative circumstances but requires that additional time be spent placing the two catheters. Single catheter venous drainage from the right atrium was developed to simplify and shorten the time required for cannulation. However, the disadvantage of single catheter drainage from the right atrium only is its limitation to those procedures not requiring the previously discussed operative manipulations which reduce the blood flow. A two-stage catheter has also been developed to combine the desirable simplicity, convenience, and time savings of the single catheter with the higher reliability of the two catheter technique.

It is an object of the present invention to provide a single stage venous catheter which achieves the advantages of the double catheter on the two-stage catheter, which is easily installed and which insures adequate drainage during a heart operation. It is a further object to provide a catheter designed for maximum flow and one which can be installed with a minimal loss of blood and through a single aperture created by the amputation or incision of a portion of the distal appendage.

One type of two-stage catheter is disclosed in U.S. Pat. No. 4,129,129, issued to Bruce A. Amrine on Dec. 12, 1978. The present invention relates to a simplified catheter construction which is readily molded in a one-piece unit and which performs the function of a two-point pick up while eliminating the more complex internal passages.

Other objects and features of the invention will be apparent in the following detailed description and claims in which there is set forth the invention together with details to enable a person to practice the invention, all in connection with the best mode presently contemplated for the invention.

DRAWINGS accompany the disclosure and the various views thereof may be briefly described as:

FIG. 1, an elevation of the entire catheter.
FIG. 2, an end view on line 2—2 of FIG. 1.
FIG. 3, a sectional view on line 3—3 of FIG. 1.
FIG. 4, a sectional view on line 4—4 of FIG. 1.
FIG. 5, a partial longitudinal section of FIG. 1 through a narrow fin centrally of the catheter.
FIG. 6, a sectional view on line 6—6 of FIG. 1.
FIG. 7, a sectional view on line 7—7 of FIG. 1.
FIG. 8, an elevation of the insertion end of the catheter with a spiral flute.

WITH REFERENCE TO THE DRAWINGS, in FIG. 1, an elevation of the single stage venous catheter is shown. The section 10 bracketed as A is composed of four fins 12 each 90° apart joined at the axis. FIG. 2 illustrates the end view of the cannula showing the fins 12. FIG. 4 illustrates the sectional view of these fins 12. The tip of this section of the cannula tapers at 14 to a rounded end 16. Thus, this portion of the cannula forms longitudinally extending open-sided sectorial passages around a common axis.

The bracketed section B in FIG. 1 shows the fins 12 enlarging in diameter and thickness to fins 20 up to a root section 22 of the cannula with a slight decrease in diameter past the point 24. This is illustrated in the end view of FIG. 2.

With further reference to section B of the cannula, four additional fins 30 originate at the root section 22 extending away from the root section toward the tip 16. Four of these fins 30 are located half-way between fins 20 bisecting the 90° angle between fins 20. These fins 30 extend toward the tip a little beyond the point 24 and are shown in sectional view FIG. 6.

Eight shorter fins 40 bisect the space between fins 20 and 30, these terminating short of the point 24. Sectional view FIG. 7 shows these fins 40.

The root section 22 shown in section in FIG. 5 has a fist circular opening 42 to receive the end of tubing 44 leading to the life support system. An opening 52 of smaller diameter provides a shoulder 54 against which the end of the tubing can abut. The opening 52 provides a clear passage from the tubing to the sectorial passages 60 between fins 20-12 as shown in FIGS. 2 and 3.

It will be noted that, while fins 12-20 extend to a common axis of the cannula, the shorter fins 30 and 40 have an inner diameter terminating at the inner diameter of the opening 52.

In the use of the above-described single stage venous catheter, an opening into the heart is surgically instituted as is the practice in open heart surgery. The catheter is inserted into the atrium of the heart toward the inferior vena cava. Both the the tip 16 and the root 22 should be inserted smoothly and quickly to minimize blood loss. The distal tip 16 is advanced into the inferior vena cava, thus positioning the root section 22 into the right atrium. This permits collection of blood from the coronary sinus and venous return from the superior vena cava. The webs or fins 12 at the tip end 26 keep the inferior vena cava open and flow will occur along the four sectorial channels between the fins 12. The ribs or fins 30 prevent the atrium from collapsing over the opening 52 in the root 22 and thus prevent blocking of flow.

The area of the catheter at the root 22 and the fins 30 and 40 is sometimes referred to as the basket area of the cannula. With the single basket area in the cannula, there is no pressure drop in the open fin section and thus flow is significantly improved with the use of the finned section A.

The material from which the catheter is formed is preferably a flexible plastic molded to the proper shape and dimensions with suitable fillets and no sharp corners.

In FIG. 8, a modified form of the catheter is illustrated in which the insertion end is shaped such that fins 12' have a spiral shape to facilitate insertion and flow.

What I claim is:

1. A single stage venous return catheter for insertion into the right atrium and inferior vena cava of the heart to drain blood of the patient to an extracorporeal life support machine which comprises:
   (a) an integral penetration section composed of a plurality of elongate first fins disposed around a common axis forming elongate open-sided sector passages between the fins,
   (b) a root section integral with one end of said penetration section having an end to connect to a connector tube and having an axial opening in alignment with and in communication with the elongate sector passages between said fins, and
   (c) a series of axially extending second fins on said root section extending toward said penetration section outside the sector passages between said first fins.

2. A single stage venous return catheter as defined in claim 1 in which a plurality of third fins are spaced around said root sections between said first and second fins.

3. A single stage venous return catheter as defined in claim 1 in which said first fins enlarge radially as they approach the root section to a diameter about the same as that of said root section.

4. A single stage venous return catheter as defined in claim 1 in which said first fins enlarge radially and become circumferentially thicker as they approach the root section, the radial enlargement being to a diameter about the same as that of said root section.

5. A single stage venous catheter as defined in claim 1 in which said elongate firsts fins are disposed in a spiral shape around the common axis.

* * * * *